United States Patent
Cho et al.

(10) Patent No.: US 8,221,701 B2
(45) Date of Patent: Jul. 17, 2012

(54) CENTRIFUGAL FORCE-BASED MICROFLUIDIC DEVICE FOR BLOOD CHEMISTRY ANALYSIS

(75) Inventors: Yoon-kyoung Cho, Suwon-si (KR);
Do-gyoon Kim, Yongin-si (KR);
Jung-nam Lee, Incheon (KR);
Hee-kyun Lim, Hwaseong-si (KR)

(73) Assignee: Samsung Electronics Co., Ltd., Suwon-si (KR)

( * ) Notice: Subject to any disclaimer, the term of this patent is extended or adjusted under 35 U.S.C. 154(b) by 0 days.

(21) Appl. No.: 12/847,076

(22) Filed: Jul. 30, 2010

(65) Prior Publication Data
US 2010/0290955 A1 Nov. 18, 2010

Related U.S. Application Data

(62) Division of application No. 12/146,523, filed on Jun. 26, 2008, now Pat. No. 7,790,110.

(30) Foreign Application Priority Data

Aug. 22, 2007 (KR) ........................ 10-2007-0084522

(51) Int. Cl.
*B01J 19/00* (2006.01)

(52) U.S. Cl. ........ 422/506; 422/500; 422/503; 422/68.1; 422/502; 422/72; 422/412; 422/64; 422/65; 422/417; 422/415; 436/45; 436/165; 436/180; 436/177; 436/175; 435/173.7; 435/286.5; 435/287.2; 435/91.2; 435/283.1

(58) Field of Classification Search ............... 422/72, 422/68.1, 61, 64, 65, 99, 100, 102, 103, 417, 422/415, 412, 502, 506, 533, 537; 435/173.7, 435/286.5, 287.2, 91.2, 89, 7.1, 6, 69.6, 283.1; 436/45, 480, 177, 175, 169
See application file for complete search history.

(56) References Cited

U.S. PATENT DOCUMENTS

| 5,693,233 A | 12/1997 | Schembri |
| 6,030,581 A | 2/2000 | Virtanen |

(Continued)

FOREIGN PATENT DOCUMENTS

| WO | 02/43866 A | 6/2002 |
| WO | 2005005045 A1 | 1/2005 |

OTHER PUBLICATIONS

"Multifunctional microvalves control by optical illumination on nanoheaters and its application in centrifugal microfluidic devices." Jong-Myeon Park, et al., Lab on a Chip, Royal Society of Chemistry, Cambridge, GB, vol. 7, Feb. 15, 2007, pp. 557-564.

(Continued)

*Primary Examiner* — In Suk Bullock
*Assistant Examiner* — Sharon Pregler
(74) *Attorney, Agent, or Firm* — Sughrue Mion, PLLC

(57) ABSTRACT

Provided is a microfluidic device that can automatically perform various types of biological blood analysis. In the microfluidic device, a specimen is centrifugally separated and the centrifugally separated specimen is diluted into various dilution ratios. Also, at least two reagents that are required for one reaction and that need to be separately stored are stored in separate chambers, and they are mixed when a reaction is needed. Thus, various conventional blood analyzing reagents can be used as they are or after being minimally processed in the microfluidic device.

2 Claims, 4 Drawing Sheets

U.S. PATENT DOCUMENTS

| | | | |
|---|---|---|---|
| 6,235,531 B1 * | 5/2001 | Kopf-Sill et al. | 422/72 |
| 7,238,269 B2 | 7/2007 | Gason et al. | |
| 7,790,110 B2 * | 9/2010 | Cho et al. | 422/72 |
| 2002/0106786 A1 * | 8/2002 | Carvalho et al. | 435/287.3 |

OTHER PUBLICATIONS

European Patent Office, Communication dated Feb. 23, 2012, issued in corresponding European application No. 12150163.9.

* cited by examiner

CENTRIFUGAL FORCE-BASED MICROFLUIDIC DEVICE FOR BLOOD CHEMISTRY ANALYSIS

CROSS-REFERENCE TO RELATED PATENT APPLICATION

The present application is a Divisional of U.S. application Ser. No. 12/146,523 filed Jun. 26, 2008 (now allowed), which claims the benefit of Korean Patent Application No. 10-2007-0084522, filed on Aug. 22, 2007, in the Korean Intellectual Property Office, the disclosures of which are incorporated herein in their entireties by reference.

BACKGROUND OF THE INVENTION

1. Field of the Invention

The present invention relates to a centrifugal force-based microfluidic device, and more particularly, to a centrifugal force-based microfluidic device that can be used for chemical analysis of blood, in which various kinds of biochemical reactions can take place using samples having different mixing ratios or reagents with different preparation conditions.

2. Description of the Related Art

A microfluidic structure that performs an independent function in a microfluidic device generally includes chambers that can contain a fluid, channels through which a fluid can flow, and valves that can control the flow of fluid. Such microfluidic structure can be configured by various combinations of the chambers, the channels, and the valves. An apparatus manufactured by disposing the microfluidic structure on a chip type substrate, so that a series of various biochemical reactions can be performed on a small chip, is referred to as a lab-on-a-chip.

In order to transport a fluid in a microfluidic structure, a driving pressure is necessary. The driving pressure can be capillary pressure or pressure supplied by an additional pump. Recently, a disk type microfluidic device in which a microfluidic structure is disposed on a disk-shaped platform to transport a fluid using centrifugal force and to perform a series of works has been proposed, which is referred to as a Lab CD (compact disk) or a Lab-on-a-disk. Efforts have been made to provide various disk types of microfluidic devices that can rapidly and accurately perform functions in a centrifugal force-based disk type platform.

Disk type microfluidic devices can be suitable for performing various kinds of pathological examinations. Conventional pathological examinations require a lot of work and various kinds of equipment. In order to rapidly perform an examination, skilled clinical pathologists are required. However, regardless of the skill of clinical pathologists, it is difficult to perform various kinds of examinations at the same time. In certain situations, for example in a diagnosis of an emergency patient, obtaining a rapid examination result is very important for rapid treatment of the patient. Thus, there is a need to develop an apparatus that can rapidly and accurately and simultaneously perform various pathological examinations.

In the case of a conventional blood test, large and expensive equipment, which requires a relatively large amount of blood, is used. Also, the patient must wait at least two to three days to receive the test result after taking a blood sample since the examination takes time. In order to address these problems, small and automated apparatuses for analyzing blood have been proposed. However, most of these apparatuses require that serum is separated from blood sample and then diluted before performing the tests.

An apparatus that can perform various kinds of biochemical reactions in different reaction conditions, requires the optimization of the concentrations of various reagents stored in reaction chambers and the amount of a diluent (or a dilution buffer). For example, according to U.S. Pat. No. 5,776,563, various kinds of reagents, which each are used in different reaction conditions, are required to be stored in a freeze-dried state until their use. The freeze-drying conditions of the individual reagents are different from each other, and thus, it has been proposed to use a reagent bead manufactured by optimizing the freeze-drying condition of each of the reagents. Furthermore, as it is difficult to provide samples diluted at different ratios, the dilution ratio of a sample is maintained constant, and the concentration or size of reagent beads and a size of a reaction chamber are varied to attain differently diluted samples. The necessity of frozen-dried reagent beads and of the reaction chambers of different sizes depending on the kind of reagents has complicated the design and construction of a microfluidic device.

Most of currently available biochemical reagents are stored and transported in a liquid state. Furthermore, in most cases, in order to preserve the reagents, individual reagents are preserved in separate containers, and then bring to mixing immediately before using. Therefore, there are many difficulties in providing a disk type microfluidic device that can use currently commercially available reagents.

SUMMARY OF THE INVENTION

To solve the above and/or other problems, the present invention provides a microfluidic device that can automatically perform various biochemical tests of a blood sample.

The present invention also provides a microfluidic device that can readily perform biochemical tests of a blood sample by using various kinds of currently commercially available reagents without or with a minimal amount of processing.

In order to achieve the above goals, the present invention also provides a microfluidic device in which reagents can be mixed in various ratios.

Also, the present invention provides a microfluidic device that can store at least two reagents in separate chambers and can mix the reagents immediately before being used.

According to an aspect of the present invention, there is provided a microfluidic device including: a rotatable platform; a specimen chamber that is disposed in the platform and accommodates a specimen injected through a specimen injection inlet; a specimen distribution unit that is disposed to be connected to the specimen chamber in the platform, centrifugally separates a specimen using the rotation of the platform, and distributes a predetermined amount of separated supernatant through a plurality of specimen distribution channels; a plurality of dilution chambers that are respectively disposed to be connected to the specimen distribution channels in the platform, store a dilution buffer, and provide diluted specimen solutions having dilution ratios different from each other by accommodating the supernatant; and a plurality of reaction chamber unit groups disposed corresponding to the plurality of dilution chambers in the platform, each of the plurality of reaction chamber unit groups comprising at least one reaction chamber unit, and wherein each reaction chamber unit group accommodates diluted specimen solution distributed from the corresponding dilution chamber of the plurality of dilution chambers through a plurality of diluted specimen distribution channels due to the rotation of the platform, and performs a reaction between a reagent stored in advance and the diluted specimen solution. The specimen distribution unit may be configured in various ways. As a first example, the specimen distribution unit may include a plurality of centrifugal separation units, each connected to the specimen chamber and centrifugally separating the specimen, wherein each of the plurality of specimen distribution channels is connected to the centrifugal separation unit. At this point, the centrifugal separation unit may include: a channel shaped supernatant collection unit extending towards an outer region of the platform from the specimen chamber; and a sediment collection unit that is disposed at an end of the supernatant collection unit to collect sediment particles, wherein the specimen distribution channel is connected to a side of the supernatant collection unit through a valve to discharge a predetermined amount of supernatant collected in an inner region of the supernatant collection unit with respect to the valve. The valve may include a valve material containing a phase change material which is a solid state at room temperature and a liquid state at high temperature and exothermic particles mixed in the phase change material, wherein the valve material opens the specimen distribution channel in a melted state due to heat generated from the exothermic particles as a result of absorbing electromagnetic waves radiated from an external energy source.

The microfluidic device may include a rotatable platform; a specimen chamber that is disposed in the platform and accommodates a specimen; a specimen distribution unit that is disposed to be connected to the specimen chamber, wherein the specimen is centrifugally separated into a supernatant and a sediment, and wherein the specimen distribution unit distributes a predetermined amount of separated supernatant through a plurality of specimen distribution channels; a plurality of dilution chambers that are respectively disposed to be connected to the respective specimen distribution channels and contain a dilution buffer, wherein the specimen flows from the specimen distribution channels into the respective dilution chambers; wherein the specimen is combined with the dilution buffer in the respective dilution chambers to provide diluted specimen solutions, each having a dilution ratio different from all or some of other diluted specimen solutions; and a plurality of reaction chamber unit groups which each are connected to the respective dilution chambers, each of the plurality of reaction chamber unit groups comprising at least one reaction chamber unit, and wherein each reaction chamber unit group contains a reagent and accommodates the diluted specimen solution distributed from the corresponding dilution chamber of the plurality of dilution chambers through a plurality of diluted specimen distribution channels due to the rotation of the platform, wherein the reagent and the diluted specimen solution are combined in the reaction chamber.

As a second example, the specimen distribution unit may include a centrifugal separation unit that is connected to the specimen chamber and centrifugally separates a specimen, and the plurality of specimen distribution channels are connected to the centrifugal separation units. At this point, the centrifugal separation unit may include: a channel shaped supernatant collection unit extending towards an outer region of the platform from the specimen chamber; and a sediment collection unit that is disposed at an end of the supernatant collection unit to collect sediment particles, wherein the plurality of specimen distribution channels are connected to the supernatant collection unit through a plurality of valves to discharge predetermined amounts of supernatant collected in inner regions of the supernatant collection unit with respect to the plurality of the valves. Also the valve may include a valve material comprising a phase change material which is a solid state at room temperature and a liquid state at high temperature and exothermic particles mixed in the phase change material, wherein the valve material opens the specimen distribution channel in a fused state due to heat generated from the exothermic particles as a result of absorbing electromagnetic waves radiated from an external energy source.

As a third example, the specimen distribution unit may include: a centrifugal separation unit that is connected to the specimen chamber and centrifugally separates the specimen; a plurality of specimen metering chambers that respectively accommodate a predetermined amount of specimen supernatant discharged from the centrifugal separation unit; and a plurality of specimen distribution channels that respectively connect the plurality of dilution chambers to the corresponding specimen metering chambers.

According to another embodiment, there is provided a rotatable platform; a specimen chamber that is disposed in the platform and accommodates a specimen; a specimen distribution unit that is disposed to be connected to the specimen chamber, wherein the specimen is centrifugally separated into a supernatant and a sediment, and wherein the specimen distribution unit distributes a predetermined amount of separated supernatant through one or more specimen distribution channels; one or more dilution chambers that are respectively disposed to be connected to the respective specimen distribution channels and serve as a container for a dilution buffer, wherein the specimen flows from the specimen distribution channels into the respective dilution chambers; wherein the specimen is combined with the dilution buffer in the respective dilution chambers to provide diluted specimen solutions, each having a dilution ratio different from all or some of other diluted specimen solutions; and a plurality of reaction chamber unit groups which each is connected to the respective dilution chambers, each of the plurality of reaction chamber unit groups comprising at least one reaction chamber unit, and wherein each reaction chamber unit group serve as a container for a reagent and accommodate the diluted specimen solution distributed from the corresponding dilution chamber of the plurality of dilution chambers through a plurality of diluted specimen distribution channels due to the rotation of the platform, wherein the reagent and the diluted specimen solution are combined in the reaction chamber.

The diluted specimen distribution channels may include: a distribution section that is connected to the dilution chamber through a valve and extends along a circumference direction of the platform; at least one vent connected to the distribution section; and a plurality of inlet channels branched to the plurality of reaction chamber units that belong to the reaction chamber group from the distribution section.

At least one of the reaction chamber units may include: a metering chamber that is connected to an inlet channel branched from the diluted specimen distribution channel to accommodate a predetermined amount of diluted specimen and includes valve at an outlet thereof; a first reaction chamber that is connected to an outlet of the metering chamber, stores a first reagent, and comprises a valve at an outlet thereof; and a second reaction chamber that is connected to an outlet of the first reaction chamber and stores a second reagent. Also, in this case, the valve comprises a valve material comprising a phase change material which is a solid state at room temperature and a liquid state at high temperature and exothermic particles mixed in the phase change material, wherein the valve material opens the diluted specimen distribution channel in a fused state due to heat generated from the exothermic particles as a result of absorbing electromagnetic waves radiated from an external energy source.

According to an aspect of the present invention, there is provided a microfluidic device including: a rotatable platform; a specimen chamber that is disposed in the platform and accommodates a specimen injected through a specimen injection inlet; a specimen distribution unit that is disposed to be connected to the specimen chamber in the platform, centrifugally separates a specimen using the rotation of the platform, and distributes predetermined amounts of separated supernatant through a specimen distribution channel; a dilution chamber that is disposed to be connected to the specimen distribution channel in the platform, stores a dilution buffer, and provides a diluted specimen solution having a predetermined dilution ratio by accommodating the supernatant; and a plurality of reaction chamber units that are connected to the dilution chamber in the platform through a diluted specimen distribution channel, accommodate diluted specimen distributed by the rotation of the platform, and in which a reaction between the distributed diluted specimen and a reagent stored in advance is performed, wherein at least one of the reaction chamber units comprises: a metering chamber that is connected to an inlet channel branched from the diluted specimen distribution channel to accommodate a predetermined amount of diluted specimen and comprises a valve at an outlet thereof; a first reaction chamber that is connected to an outlet of the metering chamber, stores a first reagent, and comprises a valve at an outlet thereof; and a second reaction chamber that is connected to an outlet of the first reaction chamber and store a second reagent.

The specimen distribution unit may include a centrifugal separation unit that is connected to the specimen chamber and centrifugally separates a specimen, and the specimen distribution channel is connected to the centrifugal separation unit. The centrifugal separation unit includes: a channel shaped supernatant collection unit extending towards an outer region of the platform from the specimen chamber; and a sediment collection unit that is disposed at an end of the supernatant collection unit to collect sediment particles, wherein the specimen distribution channel is connected to a side of the supernatant collection unit through a valve to discharge a predetermined amount of supernatant collected in an inner region of the supernatant collection unit with respect to the valve. At this point, each of the valves comprises a valve material comprising a phase change material which is a solid state at room temperature and a liquid state at high temperature and exothermic particles mixed in the phase change material, wherein the valve becomes in a opened state in a fused state due to heat generated from the exothermic particles as a result of absorbing electromagnetic waves radiated from an external energy source.

The diluted specimen distribution channel may include: a distribution section that is connected to the dilution chamber through a valve and extends along a circumference direction of the platform; at least one vent connected to the distribution section; and a plurality of inlet channels branched towards the plurality of reaction chamber units that belong to the reaction chamber group from the distribution section.

BRIEF DESCRIPTION OF THE DRAWINGS

The above and other features and advantages of the present invention will become more apparent by describing in detail exemplary embodiments thereof with reference to the attached drawings in which.

DETAILED DESCRIPTION OF THE INVENTION

The present invention will now be described more fully with reference to the accompanying drawings in which exemplary embodiments of the invention are shown.

While the description of the invention focuses on the blood analysis, the device of the invention are suitable for the analysis of any liquid, typically a biological sample such as whole blood or plasma, urine, sputum, semen, saliva, ocular lens fluid, cerebral fluid, spinal fluid, amniotic fluid.

Figure 1:
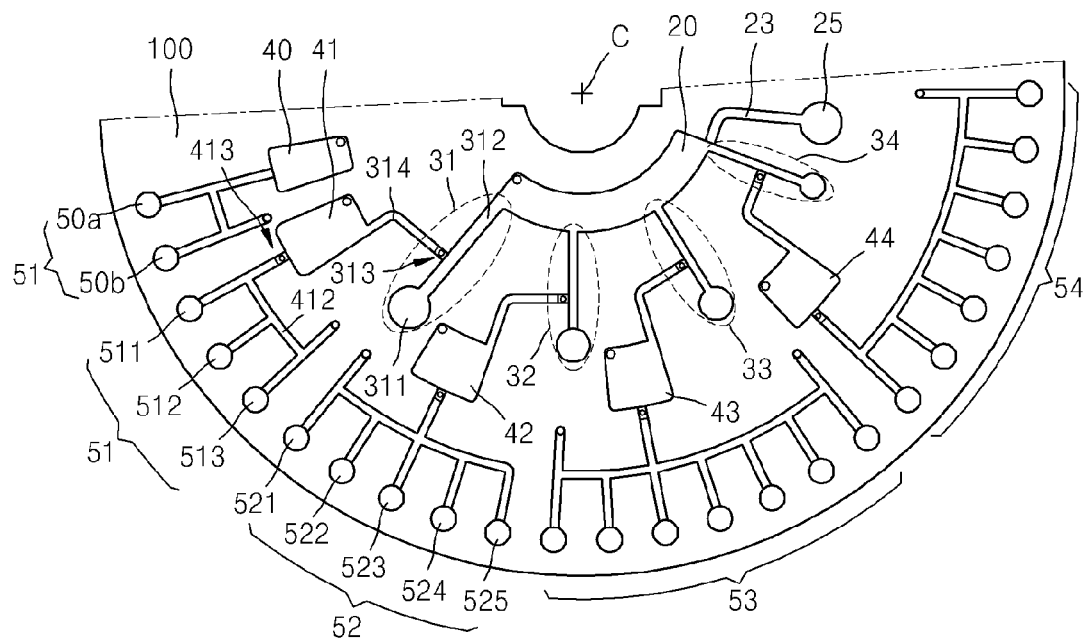
FIG. 1 is a plan view of a microfluidic device for blood analysis, according to an embodiment of the present invention.

FIG. 1 is a plan view of a centrifugal force-based microfluidic device for blood analysis according to an embodiment of the present invention. The centrifugal force-based microfluidic device includes a rotatable platform 100 and structures that provide spaces for accommodating fluids and flow channels through which the fluids can flow. The disk type platform 100 can be a shape of a disk and rotated with respect to the center C thereof. In the structures disposed in the disk type platform 100, moving of a specimen, centrifugal separation, and mixing are performed due to the action of centrifugal force generated by the rotation of the disk type platform 100.

The disk type platform 100 can be formed of a plastic material that can be easily molded and a surface of which is biologically inactive, such as acryl or polydimethylsiloxane (PDMS). However, the material for forming the disk type platform 100 is not limited thereto, that is, any material that has chemical and biological stability, optical transparency, and mechanical processability can be used. The disk type platform 100 can comprise a plurality of plates. Spaces and paths can be provided in the disk type platform 100 by combining the plates in which engraved structures corresponding to chambers or channels are formed on surfaces of the plates such that they contact each other. The plates can be combined using various methods such as using an adhesive or a dual-sided adhesive tape, ultrasonic wave fusion bonding, or laser welding.

Structures disposed in the disk type platform 100 for blood tests are described. Here, an area close to the center of the disk type platform 100 is referred to as an inner region, and an area farther from the center of the disk type platform 100 is referred to as an outer region. A specimen chamber 20 is disposed in the innermost region of the disk type platform 100. A blood is introduced and stored in the specimen chamber 20 through a specimen inlet. In FIG. 1, the specimen inlet is shown to be located in a left upper side of the specimen chamber 20. A surplus specimen chamber 25 connected to the specimen chamber 20 through a channel 23 can be disposed on a side of the specimen chamber 20. If an excess amount of specimen is loaded into the specimen chamber 20, a specimen required for tests is stored in the specimen chamber 20, and the surplus amount may be stored in the surplus specimen chamber 25.

A specimen distribution unit connected to the specimen chamber 20 is disposed radially outward of the specimen chamber 20. The specimen distribution unit centrifugally separates the specimen using the rotation of the disk type platform 100, and distributes a desired amount of supernatant separated by the centrifugal force, through a plurality of supernatant distribution channels. The specimen distribution unit can be configured in various ways, and a first exemplary embodiment is shown in FIG. 1. Referring to FIG. 1, a plurality of centrifugal separation units 31 through 34 connected to the specimen chamber 20 are disposed radially outward of the specimen chamber 20. The centrifugal separation units 31 through 34 may have an identical configuration. The centrifugal separation unit 31 among the centrifugal separation units 31 through 34 will now be described as an example. The centrifugal separation unit 31 includes a channel-shaped supernatant collection unit 312 extending radially outwards from the specimen chamber 20 and a sediment (precipitant) collection unit 311 disposed radially outward of the supernatant collection unit 312. The sediment collection unit 311 receives and stores sediments having a large specific gravity. A specimen distribution channel 314 that distributes collected supernatant to a next stage structure may be is disposed on a side of the supernatant collection unit 312. The specimen distribution channel 314 is connected to the supernatant collection unit 312 through a valve 313. At this point, the location where the specimen distribution channel 314 is connected to the supernatant collection unit 312 may vary according to the amount of specimen to be distributed. That is, the amount of specimen to be distributed is determined according to the volume of specimen located in radially inward region of the supernatant collection unit 312 with respect to the valve 313. The valve 313 may be of various types of microfluidic valves. For example, a capillary tube valve that is passively opened when a pressure greater than a predetermined pressure is applied can be employed, or a valve that is actively operated by receiving energy or power in response to an operational signal can be employed. In the present embodiment, a phase change valve (refer to FIG. 4) that is operated by absorbing electromagnetic wave energy from the outside is employed. The operation and configuration of the phase change valve will be described later.

A plurality of dilution chambers 41 through 44 corresponding to the centrifugal separation units 31 through 34 are respectively disposed radially outward of the centrifugal separation units 31 through 34. The plurality of dilution chambers 41 through 44 accommodate specimen (specifically, the supernatant centrifugally separated from the specimen) distributed from the centrifugal separation units 31 through 34, respectively. Different kinds or volumes of dilution buffers (or diluents) are respectively stored in the dilution chambers 41 through 44. The volumes of the dilution chambers 41 through 44 can be varied according to the volumes of the required dilution buffers. Thus, the dilution chambers 41 through 44 provide specimen diluted to different concentrations or with a different diluent. In order to produce specimen diluted to different ratios, the volumes of the dilution buffers stored in the dilution chambers 41 through 44 can be adjusted, and/or the amount of specimen distributed from the specimen distribution unit can be adjusted. The dilution ratio or the concentration of the diluted specimen prepared and stored in individual dilution chambers may different from each other. An additional dilution chamber 40 ("auxiliary dilution chamber" or "dummy dilution chamber") that stores a dilution buffer and does not receive specimen from the specimen distribution unit, can be provided. The dilution buffer stored in the auxiliary dilution chamber 40 may be used for obtaining a detection reference value. The auxiliary dilution chamber 40 may be connected to chambers 50a and 50b, which may be kept empty or receive the dilution buffer. The chambers 50a and 50b are positioned radially outward of the auxiliary dilution chamber 40 that does not receive the specimen. The reaction chambers 50a and 50b can be vacant or filled with distilled water.

Reaction chamber unit groups 51 through 54 that respectively correspond to the dilution chambers 41 through 44 are disposed radially outward of the respective dilution chambers 41 through 44. The reaction chamber unit group (a first group) 51 will now be described as an example of the reaction chamber unit group. The reaction chamber unit group 51 includes at least one reaction chamber units. In FIG. 1, numerical references 511 through 513 indicates reaction chamber units, and the reaction chamber units 511 through 513 are connected to the corresponding dilution chamber 41 through a diluted specimen distribution channel 412. For a simple operation, one reaction chamber unit may be formed, instead of plural reaction chambers. As depicted in FIG. 1, the diluted specimen distribution channel 412 can include a compartment that is connected to the dilution chamber 41 interposing a valve 413 therebetween and extend radially outwards from the dilution chamber 41, a distribution compartment extending in a circumferential direction of the disk type platform 100, a vent connected to an end of the distribution compartment, and a plurality of inlet channels branched outwards from the distribution compartment and connected to the corresponding reaction chamber units 511 through 513. The reaction chamber units 511 through 513 each may have identical capacity and shape, or different capacity and/or shape from the others. The capacity and shape may be determined by one skilled in the art depending on the specimen to be tested or the purpose of the tests.

Reagents that reaction with specimen (blood) are stored in the reaction chamber units 511 through 513. Different reagents may be stored in each of individual reaction chambers 511 to 513 for reactions with a diluted specimen flown from the dilution chamber 41. The next group of reaction chambers (e.g., "group 52" in FIG. 1) may contain reagents which each are the same to or different from the those contained in reaction chambers 511 to 513 ("group 51" in FIG. 1). The kind of reagents to be contained in each of the reaction chambers may be decided by one skilled in the art depending on the types of the specimen or target components to be detected/measured.

For example, when the a blood sample is tested for detecting/measuring alanine aminotransferase (ALT) and aspartate aminotransferase (AST), the blood sample needs to be diluted to 10 times for the testOn the other hand, if a blood sample is tested for directing bilirubin (DBIL), total bilirubin (TBIL), and gamma glutamyl transferase (GGT), the dilution ratio is 20. If the test is to detect and/or measure uric acid (UA), alkaline phosphatase (ALP), amylase (AMY), and creatin kinase (CK), the dilution ratio is 50. Furthermore, if the test is to detect/measure triglycerides (TRIG), total cholesterol (Chol), glucose (GLU), and urea nitrogen (BUN), the dilution ratio is 100. If the disk type microfluidic device according to the present invention is used, all or some of the above components may be efficiently detected/measured at once on a single device, by providing specimen solutions diluted by the same ratio into a group of reaction chambers (e.g., 10 times diluted specimen solutions are distributed to the group 51 of reaction chambers 511-513, and 20 times diluted specimen solutions are distributed to the group 52 of reaction chambers 521-525, and so on). This can be attained by adjusting the location of the distribution channel (e.g., 314) or the amount of a diluent loaded in the dilution chamber (e.g., 41). In this manner, currently available biochemical reagents for analyzing blood can be used without additional processing, such as freeze-drying.

Each of the reaction chamber units 511 through 513 and 521 through 525 can include one closed reaction chamber. In each of the closed reaction chambers, reagents required for each of the examination reactions is stored. The reagents can be filled in the closed reaction chambers during the manufacture of the disk type microfluidic device prior to combining an upper plate and a lower plate that constitute the disk type platform 100. Conventional liquid state reagent can be used. A distribution structure (for example, the diluted specimen distribution channel 412) for distributing a fluid into the multiple closed reaction chambers has been described in detail in co-pending application Ser. No. 12/108,823. However, the present invention is not limited to the above distribution structure. In the above distribution structure, a solid state reagent can also be used as well as a liquid state reagent. Also, each of the reaction chamber units 511 through 513 and 521 through 525 may have a reaction chamber having a vent and an inlet instead of the closed reaction chamber. Furthermore, the flow of the specimen and diluted specimen may further be controlled by way of a valve located on the channels through which the specimen and diluted specimen flow. In FIG. 1, the numerical number 313 indicates one of the valves.

Figure 2:
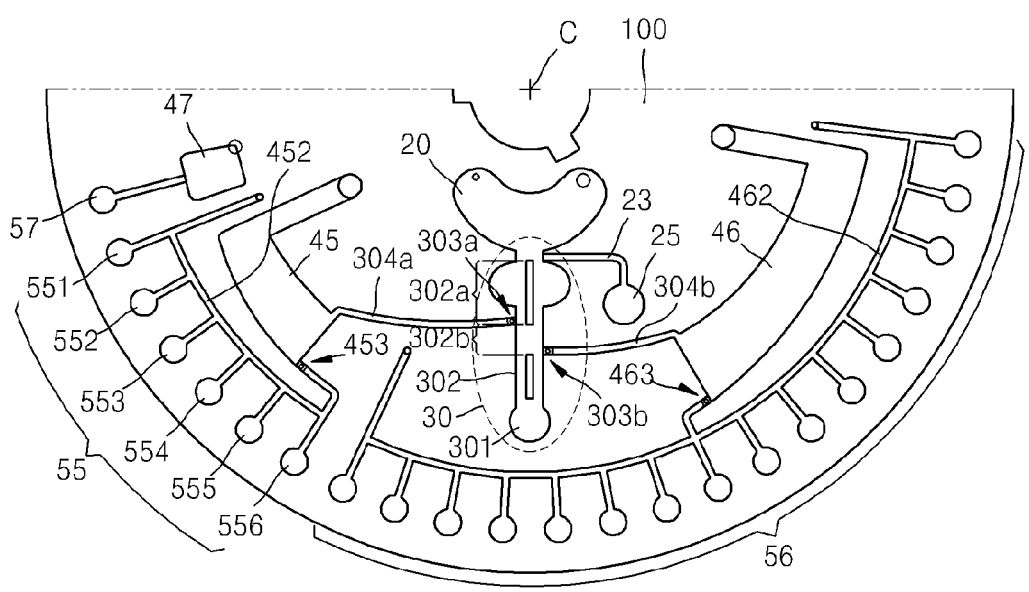
FIG. 2 is a plan view of a microfluidic device for blood analysis according to another embodiment of the present invention.

FIG. 2 is a plan view of a microfluidic device for blood analysis according to another embodiment of the present invention. In the present embodiment, unlike the specimen distribution unit in FIG. 1, a specimen distribution unit can be configured such that one centrifugal separation unit 30 is connected to a plurality of specimen distribution channels 304a and 304b. The one centrifugal separation unit 30 also includes a supernatant collection unit 302 extending outwards from the specimen chamber 20 and a sediment collection unit 301 disposed on an end of the supernatant collection unit 302. The supernatant collection unit 302 may have a channel shape and a width and depth of the supernatant collection unit 302 can be modified according to the amount of specimen to be treated.

A plurality of specimen distribution channels 304a and 304b (for example, two specimen distribution channels in FIG. 2) are connected to different positions of the supernatant collection unit 302. That is, specimen distribution channel 304a is positioned radially inward of the other specimen distribution channel 304b. There are valves 303a and 303b each located between the supernatant collection unit 302 and the channel 304a, and between the unit 302 and the channel 304b, respectively. The two valves 303a and 303b may be independently operated, and preferably, the valve 303a disposed close to the center of the disk type platform 100 may be operated prior to the operation of the valve 303b. When the disk type platform 100 is rotated and the valve 303a opens, the specimen placed in a portion 302a which is positioned in the supernatant collection unit 302 radially inward of the valve 303a is discharged through the valve 303a into the specimen distribution channel 304a. Next, when the disk type platform 100 is rotated and the valve 303b opens, the specimen placed in a portion 302b which is between the valve 303a and the valve 303b is discharged through the specimen distribution channel 304b into the specimen distribution channel 304b. The centrifugal separation unit 30 having the above configuration separates a specimen that includes particles into a fluid (supernatant) and particles (sediments), and the separated supernatant can be divided into predetermined volumes (respectively, to volumes of 302a and 302b) to distribute. A microfluidic structure for centrifugal separation and quantitative distribution of a specimen has been described in detail in co-pending application Ser. No. 12/056,345.

The two volumes of the specimen distributed from the single centrifugal separation unit 30 are respectively transported to two dilution chambers 45 and 46 which have different volumes from each other and are mixed with a dilution buffer stored in advance in each of the chambers. Specimen dilution solution that have different dilution ratios from each other and are distributed from the dilution chambers 45 and 46 through valves 453 and 463 respectively are distributed to corresponding reaction chamber groups 55 and 56 through specimen distribution channels 452 and 462. In the present embodiment, in a plurality of reaction chamber units 551 through 556 that belong to a reaction chamber group 55 corresponding to the dilution chamber 45, reagents for blood tests, for example, ALT, AST, GGT, DBIL, and TBIL, which require the dilution ratio of dilution buffer/supernatant according to a commercialized reaction condition of 10, can be stored in advance. Also, in a reaction chamber group 56 corresponding to the dilution chamber 46, reagents for blood examination items, for example, BUN, CK, LD, ALP, AMY, CHIL, GLU, TRIG, and UA, which require the dilution ratios of dilution buffer/supernatant according to a commercially available reaction condition of 100, can be stored in advance. The structural characteristics and functions of the diluted specimen distribution channels 452 and 462 and the reaction chamber units 551 through 556 are the same as the diluted specimen distribution channel 412 and the reaction chamber units 511 through 513 and 521 through 525 described with reference to FIG. 1. Like the auxiliary dilution chamber 40 and the reaction chambers 50a and 50b in FIG. 1. an additional dilution chamber 47 ("auxiliary dilution chamber 47" or "dummy dilution chamber 47") into which a specimen is not distributed and a reaction chamber 57 connected to the auxiliary dilution chamber 47 may also be provided to obtain a detection reference value.

Figure 3:
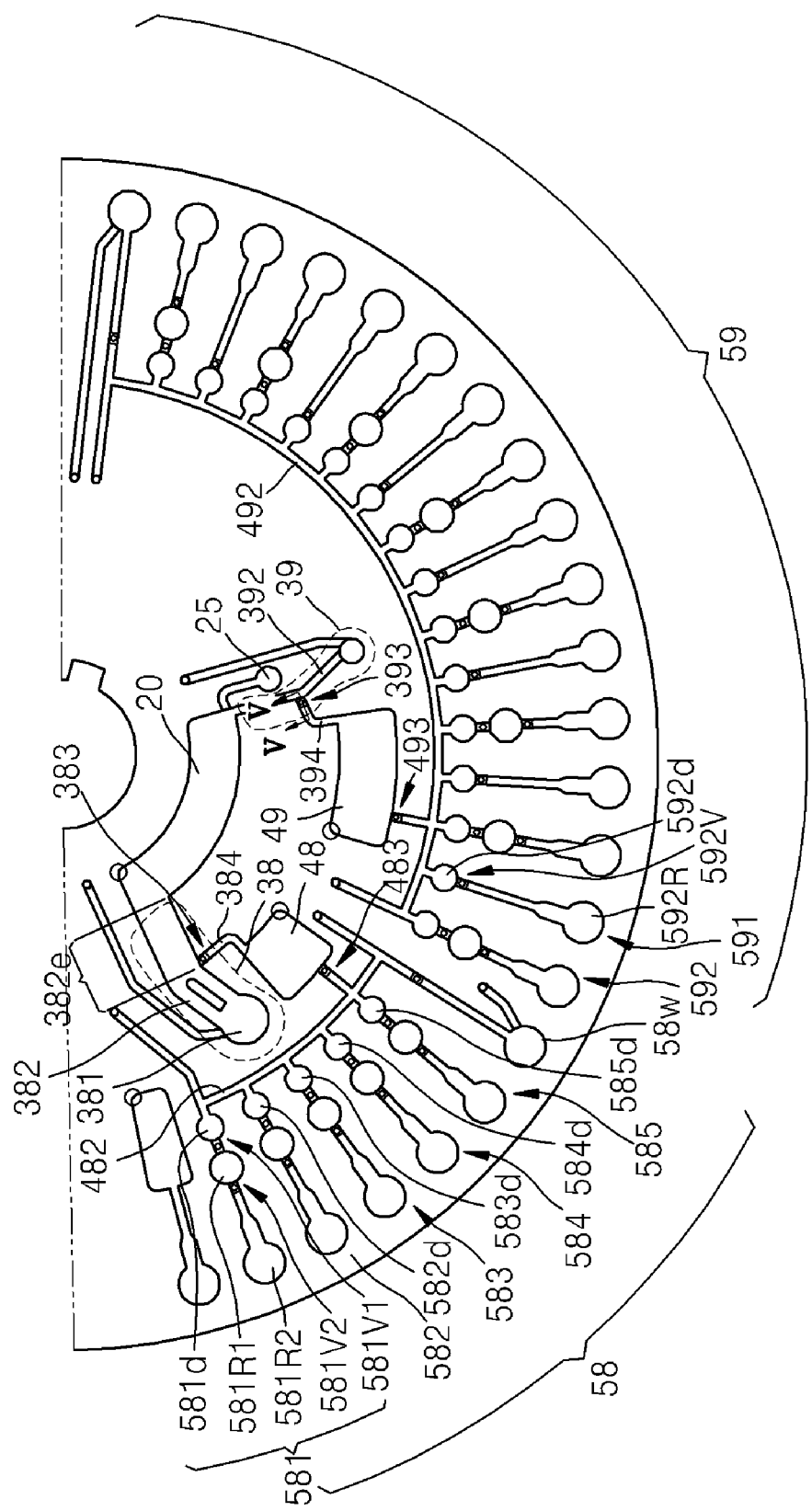
FIG. 3 is a plan view of a microfluidic device for blood analysis according to another embodiment of the present invention.

FIG. 3 is a plan view of a microfluidic device for blood analysis according to another embodiment of the present invention. The microfluidic device according to the present embodiment includes a specimen distribution unit having a plurality of centrifugal separation units 38 and 39 as in FIG. 1. In FIG. 3, a supernatant collection unit 382 of the centrifugal separation unit 38 has a cross-sectional area which is greater than that of a supernatant collection unit 392 of the centrifugal separation unit 39. Thus, the centrifugal separation unit 38 can supply a relatively large volume 382a of a specimen to a dilution chamber 48 which is connected to the centrifugal separation unit 38 through a valve 383. A relatively small volume of specimen is supplied to a dilution chamber 49 connected to the centrifugal separation unit 39 through a valve 393. In this manner, by differentiating the volumes of the centrifugal separation units 38 and 39, the ratio of dilution buffer/supernatant (i.e., dilution ratio) can be differentiated. At this point, the volumes of the dilution buffer loaded in advance and stored in the two dilution chambers 48 and 49 may also be different from each other. A configuration for distributing the diluted specimen of different dilution ratios from the two dilution chambers 48 and 49 to reaction chamber unit groups 58 and 59 through respective valves 483 and 493 and diluted specimen distribution channels 482 and 492 is the same as the configurations described with reference to FIGS. 1 and 2.

However, the reaction chamber unit 58 (and 59) according to the present embodiment has a different configuration from the reaction chamber unit groups 51, 52 and 55 in FIGS. 1 and 2. All or some of a plurality of reaction chamber units 581 through 585, includes first and second reaction chambers 581R1 and 581R2 that can be separated from each other by a valve 581V2. In an exemplary embodiment depicted in FIG. 3, all of reaction chambers 581-583 have two reaction chambers, while only some of reaction chambers of reaction chamber unit 59 have two reaction chambers. A first reagent R1 and a second reagent R2 can be loaded in advance and stored respectively in the first and second reaction chambers 581R1 and 581R2. At present, the majority of blood biochemical test reagents that are currently commercially available are reagents in a liquid state. Depending on the types of the tests and the target components to be detected/measured, there are many cases in which a first reagent and a second reagent need to be separately stored in order to increase preserving period. In particular, many testes require a specimen is mixed with a first reagent, followed by an incubation for a predetermined period of time, and afterwards, the second reagent is mixed with the incubated mixture of the specimen and the first reagent. For performing this type of test, the reaction chamber unit 581 may have a configuration in which the first and second reaction chambers 581R1 and 581R2 can be separated by the valve 581V2. However, the present invention is not limited to the two reaction chambers 581R1 and 581R2, that is, if three or more reagents are needed to be separately stored, the number of chambers can also be correspondingly increased. As described above, if the reagents are separately stored, even though they are in liquid state, they can be stored for approximately 18 months under a temperature condition of 2 to 10° C., which is equivalent to the preserving period of frozen condition reagents. Thus, it is not required to manufacture frozen condition reagent beads having a small volume (accurately controlled) and the difficulty in loading the solid state beads in a disk type microfluidic device can be removed. The disk type microfluidic device according to the present invention has economic feasibility and compatibility superior to a disk type microfluidic device that uses frozen condition reagent beads in that the disk type microfluidic device according to the present invention allows conventional reagents in a liquid state to be used in the automated disk type microfluidic device.

The reaction chamber unit 581 will now be described in detail. The reaction chamber unit 581 includes a metering chamber 581d that accommodates a predetermined amount of specimen dilution solution received from the inlet channel, the first reaction chamber 581R1 connected to the metering chamber 581d through a valve 581V1, and a second reaction chamber 581R2 connected to the first reaction chamber 581R1 through the valve 581V2. At this point, the two valves 581V1 and 581V2 may be separately operated from each other and independently operated from the rotation speed of the disk type platform 100. An example of the two valves 581V1 and 581V2 is a phase change valve that is separately operated using electromagnetic waves locally radiated from an external energy source. The phase change valve can prevent the first and second reagents, both in liquid state, from being mixed during centrifugally separating blood and rotating the disk type platform 100 at a high speed. The phase change valve can be employed not only between the first reaction chamber 581R1 and the second reaction chamber 581R2, but also in all positions where a valve is needed as described above in the disk type microfluidic device according to the present invention.

A reaction chamber unit 592 for a detection reaction which does not require to separately store reagents can comprise a metering chamber 592d that accommodates a desired or predetermined amount of specimen dilution solution and a reaction chamber 592R that is connected to the metering chamber 592d through a valve 592V and stores a reagent injected in advance.

Figure 4:
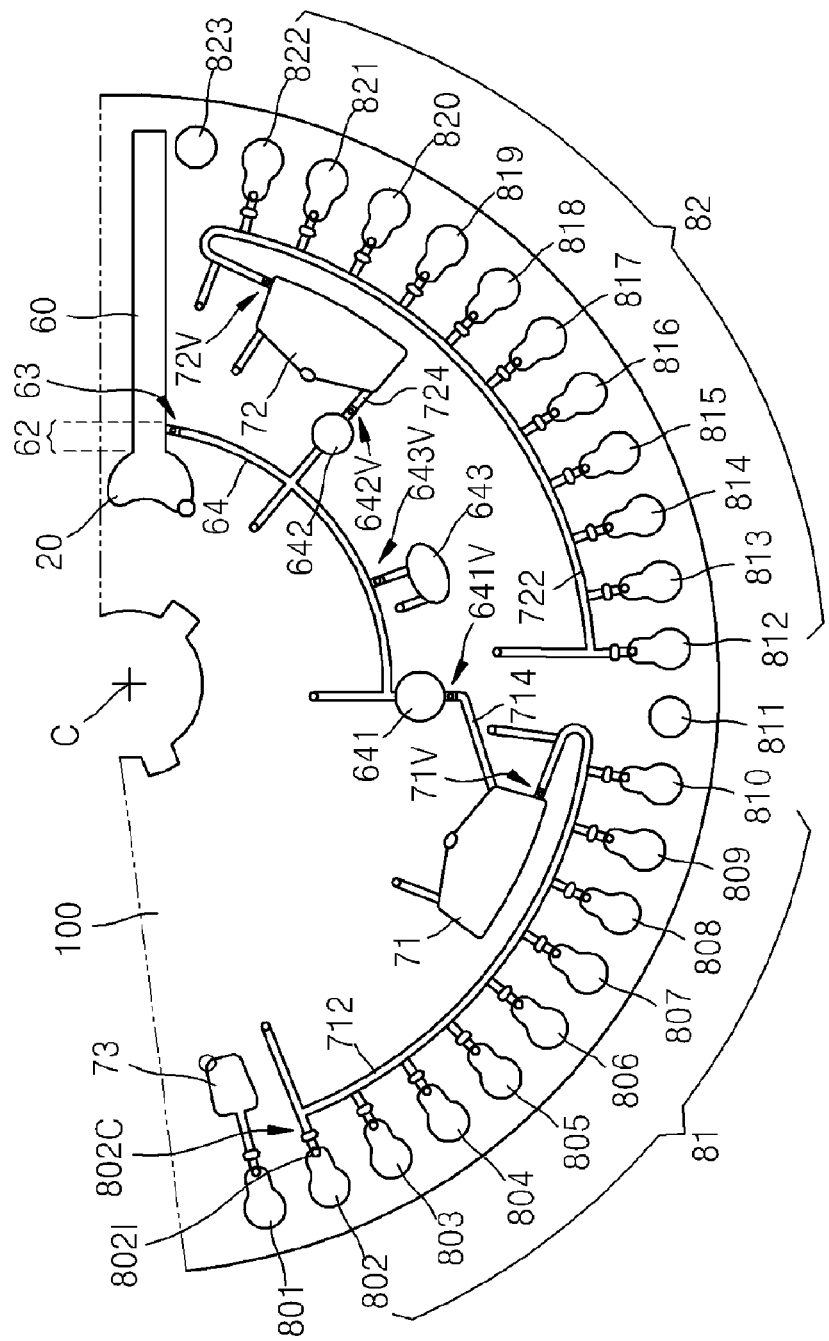
FIG. 4 is a plan view of a microfluidic device for blood analysis according to another embodiment of the present invention.

FIG. 4 is a plan view of a microfluidic device for blood analysis according to another embodiment of the present invention. The disk type microfluidic device according to the present embodiment has a disk type platform 100 formed of the same material and having a shape the same as the disk type platform 100 of FIG. 1, and has the same configuration of microfluidic structures disposed in the disk type platform 100 as the configuration of microfluidic structures of FIG. 1. According to the present embodiment, a specimen chamber 20 is disposed in the disk type platform 100. A specimen distribution unit includes a centrifugal separation unit 60 that is connected to the specimen chamber 20 and centrifugally separates the specimen, a plurality of specimen metering chambers 641 and 642 that respectively accommodate a predetermined amount of specimen supernatant discharged from the centrifugal separation unit 60, and a plurality of specimen distribution channels 714 and 724 that respectively connect a plurality of dilution chambers 71 and 72 to the corresponding specimen metering chambers 641 and 642.

The specimen metering chambers 641 and 642 can accommodate a predetermined amount of specimen due to the following configuration. A channel 64 connected to a valve 63 disposed at an outlet of the centrifugal separation unit 60 has a distribution section disposed along a circumference direction of the disk type platform 100. The specimen metering chambers 641 and 642 with capacities different from each other are connected to the distribution section. If the valve 63 at the outlet of the centrifugal separation unit 60 is opened and the disk type platform 100 is rotated, specimen (more specifically, the supernatant of the specimen) collected in a supernatant collection unit 62 of the centrifugal separation unit 60 flows out through the channel 64. The specimen that flows out from the supernatant collection unit 62 fills the specimen metering chambers 641 and 642, and surplus specimen remains in the channel 64. At this point, when a valve 643V connected to the channel 64 is opened, the surplus specimen flows into a surplus specimen chamber 643. As a result, only a predetermined amount of specimen is filled in each of the specimen metering chambers 641 and 642.

Of the specimen metering chambers 641 and 642, a chamber disposed at a left side in FIG. 4 is referred to as a first specimen metering chamber 641 and a chamber disposed at a right side is referred to as a second specimen metering chamber 642. For example, the first specimen metering chamber 641 can have a capacity of 45 μl and the second specimen metering chamber 642 can have a capacity of 11 μl. The first specimen metering chamber 641 can supply the specimen (for example, serum) of 45 μl to the first dilution chamber 71 through a valve 641V disposed at an outlet of the first specimen metering chamber 641 and the specimen distribution channel 714 connected to the valve 641V. The second specimen metering chamber 642 can supply the specimen (for example, serum) of 11 μl to the second dilution chamber 72 through a valve 642V and the specimen distribution channel 724 connected to the valve 642V. A dilution buffer of 720 μl is loaded in advance and stored in the first dilution chamber 71, and a dilution buffer of 880 μl is loaded in advance and stored in the second dilution chamber 72. Thus, a specimen diluted in a ratio of 1:16 is made in the first dilution chamber 71, and a specimen diluted in a ratio of 1:80 is made in the second dilution chamber 72.

The first dilution chamber 71 distributes diluted specimen to a plurality of reaction chambers 802 through 810 that belong to a first reaction chamber unit group 81 through a valve 71V and a diluted specimen distribution channel 712. The second dilution chamber 72 distributes the diluted specimen to a plurality of reaction chambers 812 through 822 that belong to a second reaction chamber unit group 82 through a valve 72V and a diluted specimen distribution channel 722. Accordingly, diluted specimens each having different concentrations from the others are supplied to the first reaction chamber unit group 81 and the second reaction chamber unit group 82. A reagent is injected in advance into each of the reaction chambers 802 through 810 and 812 through 822. The reagent is loaded through an inlet 8021 that is connected to the reaction chamber 802. A capillary valve 802C is provided between the reaction chamber 802 and the diluted specimen distribution channel 712 to prevent the specimens loaded in advance from mixing with the specimen in the diluted specimen distribution channel 712 by flowing backward to the diluted specimen distribution channel 712.

In the present embodiment, different reagents each will be used for detecting/measuring various target components such as AST, ALT, GGT, DBIL, and TBIL can be loaded in advance into the reaction chambers 802 through 810 that belong to the first reaction chamber unit group 81. various reagents each will be used for detecting/measuring various target components such as BUN, CK, LD, ALP, AMY, GLU, CHOL, TRIG, and UA can be loaded in advance into the reaction chambers 812 through 822 that belong to the second reaction chamber unit group 82. Reagents mentioned above respectively react with a target material included in a serum specimen. The reagents are such that absorbance with respect to light having a specific wavelength varies according to concentration of the target material. Thus, the disk type microfluidic device according to the present invention can optically detect the presence and/or the quantity of the target components. Dummy chambers 811 and 823 disposed parallel to the reaction chambers 802 through 810 and 812 through 822 are for providing optical reference value for comparison. Another dummy chamber 801 disposed at a left side of FIG. 4 can provide a detection reference value with respect to a chamber filled with a dilution buffer supplied from a dilution buffer chamber 73 connected to the dummy chamber 801.

Figure 5:
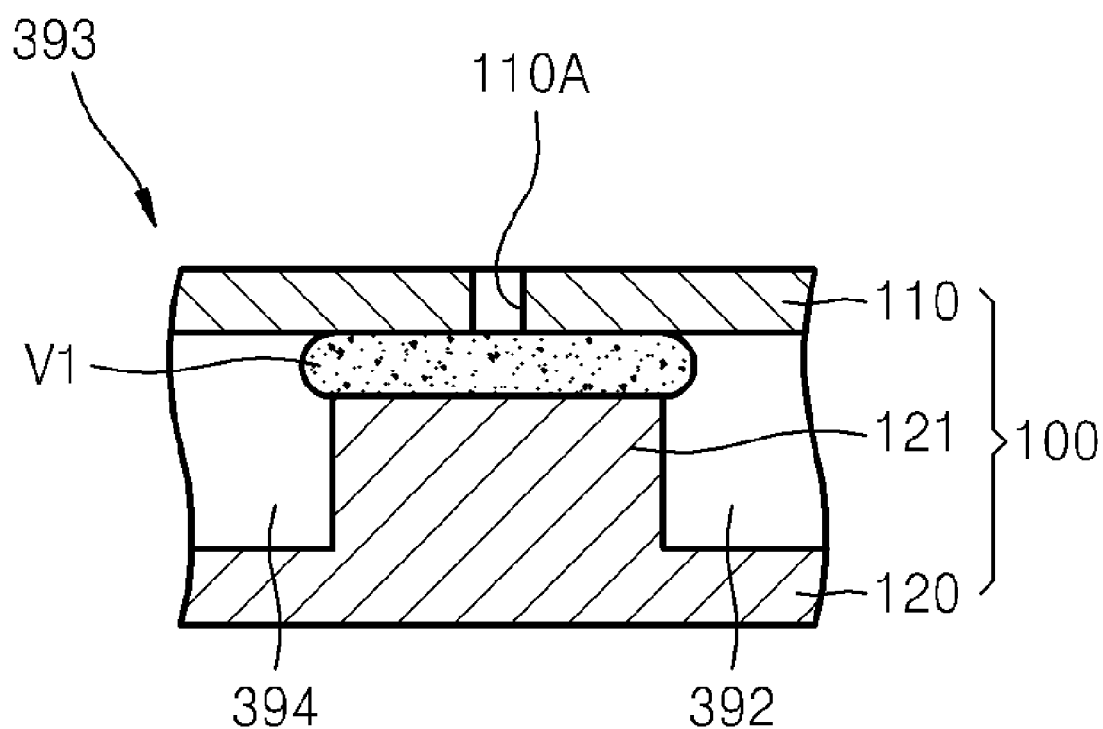
FIG. 5 is a cross-sectional view of a phase change valve employed in FIGS. 1 through 4 (shown as dot circled parts), in particular the section view taken along the line V-V' in FIG. 3, according to an embodiment of the present invention.

FIG. 5 is a cross-sectional view of a phase change valve 393 employed in FIGS. 1 through 4, according to an embodiment of the present invention. The phase change valve 393 is formed in a three-dimensional shape or a planar shape between an upper plate 110 and a lower plate 120 that constitute the disk type platform 100, and includes a valve plug (valve material) V1. The valve plug V1 is a phase change material which is a solid state at room temperature. Exothermic particles are dispersed in the phase change material. The solid state valve plug V1 is disposed in a valve gap between the upper plate 110 and a valve gap forming unit 121. The valve plug V1 is injected into the valve gap through an opening unit 110A in a melted state, and blocks fluid flow between a supernatant collection unit 392 and a specimen distribution channel 394 by solidification. The valve plug V1 is fused at a high temperature, opens the flow channel, and re-solidifies while the flow channel is opened.

In order to apply heat to the valve plug V1, an energy source (not shown) that emits electromagnetic waves is disposed outside the disk type platform 100, and the energy source can radiate electromagnetic waves on a region that includes an initial position of the valve plug V1. At this point, the energy source can be a laser light source that radiates a laser beam, a light emitting diode that radiates visible light or infrared rays, or a xenon lamp. In particular, if the energy source is a laser light source, the laser light source can include at least one laser diode. The energy source can be selected according to the wavelength of the electromagnetic waves that can be absorbed by the exothermic particles dispersed in the valve plug V1.

The exothermic particles dispersed in the valve plug V1 may have a size that can freely move in a channel having a width of a few hundred to a few thousands of micrometers. The exothermic particles generate heat to rapidly increase temperature in response to radiated electromagnetic waves (for example, a laser), and uniformly disperse in a wax. Each of the exothermic particles having the above characteristics can have a structure in which a core formed of a metal and a shell having hydrophobic characteristics are included. For example, the exothermic particle can have a structure in which a core formed of Fe and a shell formed of multiple surfactants are included. A commercially available exothermic particles in a dispersed state in a carrier oil can be employed. A valve material that forms the valve plug V1 can be made by mixing a carrier oil in which the exothermic particles are dispersed with a phase change material. The shape of the exothermic particles is not limited thereto, and can be a polymer bead, a quantum dot, or a magnetic bead.

The phase change material can be a wax. When the exothermic particles transmit absorbed electromagnetic waves to the surroundings in the form of heat energy, the wax is melted and has fluidity. Thus, the shape of the valve plug V1 is demolished to open the flow channel. The wax may have an appropriate melting point. If the melting point is too high, it takes time to melt the wax after radiating electromagnetic waves, and thus, a precise control of the opening time is difficult. If the melting point is too low, the wax can be partly melted even though the electromagnetic waves are not radiated, and thus, the fluid can leak. The wax can be a paraffin wax, a microcrystalline wax, a synthetic wax, or a natural wax. The phase change material can be a gel or a thermoplastic resin. The gel can be polyacrylamide, polyacrylates, polymethacrylates, or polyvinylamides. Also, the thermo plastic resin can be cyclic olefin copolymer (COC), polymethylmethacrylate (PMMA), polycarbonate (PC), polystyrene (PS), polyoxymethylene (POM), perfluoroalkoxy (PFA), polyvinylchloride (PVC), polypropylene (PP), polyethylene terephthalate (PET), polyetheretherketone (PEEK), polyamide (PA), polysulfone (PSU), and polyvinylidene fluoride (PVDF).

While the present invention has been particularly shown and described with reference to exemplary embodiments thereof, it will be understood by those of ordinary skill in the art that various changes in form and details may be made therein without departing from the spirit and scope of the present invention as defined by the following claims.

What is claimed is:

1. A microfluidic device comprising:
    a rotatable platform;
    a specimen chamber that is disposed in the platform and accommodates a specimen;
    a specimen distribution unit that is disposed to be connected to the specimen chamber, wherein the specimen is centrifugally separated into a supernatant and a sediment, and wherein the specimen distribution unit distributes a predetermined amount of separated supernatant through specimen distribution channels;
    a plurality of dilution chambers that are respectively disposed to be connected to the respective specimen distribution channels and serve as a container for a dilution buffer, wherein the specimen flows from the specimen distribution channels into the respective dilution chambers, and wherein the specimen is combined with the dilution buffer in the respective dilution chambers to provide diluted specimen solutions, each having a dilution ratio different from all or some of other diluted specimen solutions; and
    a plurality of reaction chamber unit groups which each is connected to the respective dilution chambers, each of the plurality of reaction chamber unit groups comprising at least one reaction chamber unit, and wherein each reaction chamber unit group serves as a container for a reagent and accommodate the diluted specimen solution distributed from the corresponding dilution chamber of the plurality of dilution chambers through a plurality of diluted specimen distribution channels due to the rotation of the platform, wherein the reagent and the diluted specimen solution are combined in the reaction chamber, wherein the plurality of dilution chambers comprises a first chamber having a first volume and a second chamber having a second volume, said second volume being less than the first volume.

2. A microfluidic device comprising:

a rotatable platform;

a specimen chamber that is disposed in the platform and accommodates a specimen;

a specimen distribution unit that is disposed to be connected to the specimen chamber, wherein the specimen is centrifugally separated into a supernatant and a sediment, and wherein the specimen distribution unit distributes a predetermined amount of separated supernatant through specimen distribution channels;

a plurality of dilution chambers that are respectively disposed to be connected to the respective specimen distribution channels and serve as a container for a dilution buffer, wherein the specimen flows from the specimen distribution channels into the respective dilution chambers, and wherein the specimen is combined with the dilution buffer in the respective dilution chambers to provide diluted specimen solutions, each having a dilution ratio different from all or some of other diluted specimen solutions; and a plurality of reaction chamber unit groups which each is connected to the respective dilution chambers, each of the plurality of reaction chamber unit groups comprising at least one reaction chamber unit, and wherein each reaction chamber unit group serves as a container for a reagent and accommodate the diluted specimen solution distributed from the corresponding dilution chamber of the plurality of dilution chambers through a plurality of diluted specimen distribution channels due to the rotation of the platform, wherein the reagent and the diluted specimen solution are combined in the reaction chamber, wherein the specimen distribution channels comprise a first specimen distribution channel connected to the specimen distribution unit at a first radial distance from the center of the rotatable platform, and a second specimen distribution channel connected to the specimen distribution unit at a second radial distance from the center of the rotatable platform, said second radial distance being less than the first radial distance.

* * * * *